United States Patent [19]
Durand et al.

[11] Patent Number: 5,400,784
[45] Date of Patent: Mar. 28, 1995

[54] SLOWLY PENETRATING INTER-FASCICULAR NERVE CUFF ELECTRODE AND METHOD OF USING

[75] Inventors: Dominique J. Durand, Solon; Dustin J. Tyler, Cleveland, both of Ohio

[73] Assignee: Case Western Reserve University, Cleveland, Ohio

[21] Appl. No.: 138,237

[22] Filed: Oct. 15, 1993

[51] Int. Cl.$^6$ .................... A61B 5/04; A61N 1/05
[52] U.S. Cl. .................... 128/642; 607/118; 29/825
[58] Field of Search .............. 607/117, 118, 152, 116, 607/130, 149; 128/642, 644, 741; 29/825, 832, 835

[56] References Cited

U.S. PATENT DOCUMENTS

| | | | |
|---|---|---|---|
| 4,590,946 | 5/1986 | Loeb | 128/642 |
| 4,602,624 | 7/1986 | Naples et al. | 128/784 |
| 4,608,985 | 9/1986 | Crish et al. | 128/419 |
| 4,623,355 | 11/1986 | Sawruk | 128/642 |
| 4,628,942 | 12/1986 | Sweeney et al. | 128/784 |
| 4,649,936 | 3/1987 | Ungar et al. | 128/784 |
| 4,979,511 | 12/1990 | Terry, Jr. | 128/642 |
| 5,282,468 | 2/1994 | Klepinski | 607/118 |

OTHER PUBLICATIONS

Gregory G. Naples, et al. "A Spiral Nerve Cuff Electrode for Peripheral Nerve Stimulation", *IEEE Transactions on Biomedical Engineering*, vol. 35, No. 11 Nov. 1988, pp. 905-916.

William F. Agnew, et al. "Effects of Prolonged Electrical Stimulation of Peripheral Nerve", Chapter 6, pp. 142-167.

Gregory T. A. Kovacs, et al. "Regeneration Microelectrode Array for Peripheral Nerve Recording & Stimulation", *IEEE Transactions on Biomedical Engineering*, vol. 39, No. 9, Sep., 1992, pp. 893-902.

Robert M. Bradley, et al. "Functional Regeneration of Glossopharyngeal Nerve Through Micromachined Sieve Electrode Arrays", *Elsevier Science Publishers* pp. 84-90.

Wim L. C. Rutten, "Sensitivity and Selectivity of Intraneural Stimulation Using a Silicon Electrode Array", *IEEE Transactions on Biomedical Engineering*, vol. 38, No. 2, Feb. 1991, pp. 192-198.

Nicola Nannini, et al. "Muscle Recruitment with Intrafascicular Electrodes", *IEEE Transactions on Biomedical Engineering*, vol. 38, No. 8, Aug. 1991, pp. 769-776.

*Primary Examiner*—Lee S. Cohen
*Assistant Examiner*—Brian M. Green
*Attorney, Agent, or Firm*—Fay, Sharpe, Beall, Fagan, Minnich & McKee

[57] ABSTRACT

A self-curling sheet of a non-conductive material is biased to curl into a tight cylinder. Inwardly extending conductive members are disposed on the surface of the sheet forming the inside of the cylinder. Circumferentially separated longitudinal slices are made in the cylinder adjacent the conductive members forming spring members such that, as the sheet relaxes over time, the electrodes on the spring members engage and pierce a nerve surrounded by the cuff. The conductive segments may be electrically conductive for applying electrical impulses or fluid conductive for infusing medications. In use, a first edge of the self-curling sheet is disposed adjacent a nerve trunk which is to receive the cuff therearound. The self-curling sheet is controllably permitted to curl around the nerve into its original cylindrical shape. Over a period of a few days, electrodes riding on spring members formed by longitudinal slices into the cylinder are embedded in the nerve without damage to the perineurium membrane surrounding the nerve axons. The electrodes displace the fascicles rather than damaging them by piercing the perineurium.

49 Claims, 8 Drawing Sheets

SLOWLY PENETRATING INTER-FASCICULAR NERVE CUFF ELECTRODE AND METHOD OF USING

BACKGROUND OF THE INVENTION

The present invention relates to the biomedical arts, particularly implantable nerve cuffs for both stimulating and monitoring nerve activity. The present invention finds application in electrodes embedded in nerve trunks and other small tissue strands and will be described with reference thereto. It is to be appreciated that the invention is also applicable to medicinal infusers and other implanted biomedical devices for introducing, monitoring, or removing matter or energy.

Functional electrical stimulation of the nervous system has been shown in recent years to offer great hope in restoring some degree of lost sensory and motor function in stroke victims and individuals with spinal cord lesions. Ways in which functional electrical stimulation can be utilized to restore a particular function include:

(1) the use of surface electrodes to activate the nerves in the general region of interest;
(2) the use of intramuscular electrodes, also to activate the nerves in a general region;
(3) the use of nerve cuff electrodes placed around specific nerves of interest and used to activate them specifically; and,
(4) the use of regeneration-type neural interfaces including microelectrode arrays.

The third alternative offers advantages over the first two in that it requires the least amount of stimulating current and hence the least amount of charge injected into the tissue itself. Because the use of nerve cuff electrodes requires delicate surgery and may damage the nerves, they are usually contemplated when excitation of specific, isolated muscles is desired, or when unidirectional propagation action potentials is required.

The prior art cuff electrodes were of either the split-cylinder type or self-curling coil type. The split-cylinder type included a cylinder of dielectric material defining a bore therethrough of sufficient diameter to receive the nerve trunk to be electrically stimulated. The cylinder had a longitudinal split or opening for receiving a nerve. During installation, the longitudinal split was sutured or otherwise held closed. Although suturing held the cuff in place, an electric current path was defined through the split which permitted current leakage. Also, the suture holding the cuff closed interfered with full expansion of the cuff to accommodate swelling of the nerve. Two or three annular electrodes were positioned on the inner surface of the bore for use in applying the electrical stimuli. The electrical stimuli, for example, may provide functional electrical stimulation, may block natural nerve impulses travelling along the nerve trunk, or the like.

The self-curling type prior art cuff electrodes included a self-curling sheet of non-conductive material biased to curl into a tight spiral. A pair of conductive strips are disposed on the self-curling sheet extending peripherally around the diameter of the cuff passage. The conductive segments may be electrically conductive for applying electrical impulses or fluid conductive for infusing medications. In use, a first edge of the self-curling sheet is disposed adjacent a nerve trunk which is to receive the cuff therearound. The self-curling sheet is permitted to curl around the nerve forming an annular cuff. The effectiveness of this type of cuff is limited due to the placement of the conductive surface on the nerve rather than within the nerve.

Another prior art approach to electrical stimulation of the nervous system is a bipolar, intrafascicular electrode which penetrates the perineurium and resides within an individual fascicle of a nerve. A bipolar electrode pair is formed of two small insulated wires. The insulation is removed from the distal end of each wire. Next, the distal end of one wire is attached to an electrochemically sharpened Tungsten needle. A second wire with similar impedance is aligned with the first wire, and the two wires are threaded into a silastic tube together with a 6-0 silk thread. A small suture loop is left emerging from the distal end of the tubing to allow anchoring of the implant to the nerve. Silastic adhesive is injected into the tubing and allowed to cure. The Tungsten needle is used to thread a first (inside) wire of the electrode through the nerve fascicle for about 1 cm with the exposed zone entering this region. The second (outside) wire is not threaded through the nerve. The needle is then cut off. The other (outside) wire is placed on the outside of the fascicle, and the distal ends of the two wires are fastened to the fascicular endoneurium with a suture. The proximal end is secured in place by suturing the loop emerging from the silastic tubing to the epineurium. The tubing is led to the skin and the wound is closed, leaving the two wires accessible. This method is highly invasive and can permanently damage the nerve through penetration of the perineurium.

The basic idea behind regeneration-type neural interfaces is to manufacture a thin diaphragm with many small holes that can be positioned between the cut ends of a peripheral nerve. The nerve is left to regenerate over time through the many small holes in the diaphragm. The holes are formed by mechanical or laser drilling, or by semiconductor fabrication techniques including wet and dry etching of silicon substrate. Sophisticated interfaces include active electronics on the devices. However, although these devices are theoretically attractive, actual functionality falls short primarily because the nerves tend to regenerate around the interface rather than through it.

The present invention contemplates new and improved cuff electrodes which combine the best features of the above intrafascicular and cuff type prior art methodologies in novel ways. The improved cuffs of the present invention are readily installed without damaging the nerve trunk or other surrounding tissue.

SUMMARY OF THE INVENTION

In accordance with the present invention, a cylindrical cuff is provided for encircling and piercing a nerve trunk or other body tissue with at least one medication or electrical energy conductive member.

A first embodiment of the cuff is a split cylinder with "frayed" ends formed from non-conductive surgical tube material. The ends comprise a plurality of spring members formed by longitudinal slices into ends of the cylinder. Each of the plurality of spring members carries at least one fin member construction which in turn supports at least one medication or electrical energy conductive member. Each of the spring members are self-biased to slowly drivingly urge said fin members into the nerve trunk or other body tissue at a predetermined rate. The conductive members carried on the fin members are thus correspondingly driven into the nerve tissue. The predetermined driving rate as well as the shape of the fins are particularly selected to be slow enough and blunt enough, respectively, so that the axons within the nerve trunk are displaced rather than destroyed or pierced by the at least one medication or electrical energy conductive member. The inner diameter of the cuff in its relaxed condition is greater than the outer diameter of the target tissue providing a gap or space to accommodate swelling, etc.

Another embodiment of the cuff is a split cylinder with a "frayed" body portion intermediate the cylinder ends. Similar to the first embodiment above, the frayed body portion nerve cuff comprises a plurality of elongate spring members formed by central longitudinal slices into the cylinder. The slices extend up to but not through the cylinder ends. Each of the plurality of elongate spring members carries at least one medication or electrical energy conductive member on a fin member and is self-biased to slowly drivingly urge said fin members carrying conductive portions into the nerve trunk or other body tissue.

Control over the spring constant or force exerted by the spring members on the tissue is accomplished through a selection of non-conductive material types comprising the cylindrical body itself and the thickness, size, and dimensions of the plurality of spring members cut from the cylindrical body.

A third embodiment of the cuff includes a self-curling sheet of non-conductive material which is self-biased to slowly curl into a tight spiral or roll. The curling action of the sheet drivingly forces the at least one medication or electrical energy conductive member carried on a fin member fashioned for blunt piercing, into the nerve trunk or other body tissue. The self-curling cuff of the above-described construction is initially held flat with the fin including one or more conductive member, adjacent the body tissue to receive the cuff. Thereafter, the self-curling sheet is permitted to curl at a predetermined rate defined by the physical propertive of the cuff into a tubular spiral around the body tissue, radially inwardly driving the at least one conductive member on the fin into the nerve trunk or other body tissue. More than one fin may be provided to simultaneously urge more than one conductive member into the nerve. The inner diameter of the self curling cuff in its relaxed condition is greater than the outer diameter of the target tissue. The predetermined curl rate as well as the shape of the one or more fin members are particularly selected to be slow enough and blunt enough respectively so that the axons within the nerve trunk are displaced rather than destroyed or pierced by the at least one medication or electrical energy conductive member.

A somewhat simpler embodiment of the present invention includes one or more fin members connected to an end of a single "beam" of resilient non-conductive material. The beam is first aligned longitudinally along the direction of the nerve or other body tissue with the fin member(s) positioned facing the nerve. Next, a suture is installed over the beam and nerve tying the two together. The suture is tightened, transforming the originally flat beam into a resiliently biased curved spring. The fin members on the spring formed by the beam ends are drivingly urged into the nerve or other body tissue as the spring straightens, relaxing to its original shape.

A primary advantage of the present invention is that it can be easily installed on a nerve while providing improved electromechanical contact between the nerve trunk and the at least one medication or electrical energy conductive member.

Another advantage is that the axons and perineurium within the nerve trunk are left intact through the careful selection of the spring constant of the "frayed" cuffs or "beam" configurations and the slow rate of curl of the self-curling cuff.

Another advantage of the present invention is that a plurality of medication or electrical energy conductive members can each individually selectively communicate respective medication or electrical energy quantities to the nerve trunk at different rates and quantities simultaneously.

Another advantage of the present invention is that the various embodiments are not sensitive to variations such as expansion in the diameter of the surrounded tissue due to swelling or differences between tissue from one patient to another.

Still further advantages of the present invention will become apparent to those of ordinary skill in the art upon reading and understanding the following detailed description of the preferred embodiments.

BRIEF DESCRIPTION OF THE DRAWINGS

The invention may take form in various parts and arrangements of parts or in various steps and arrangements of steps. The Figures and the described structures and methods are only for purposes of illustrating the preferred embodiments of the invention and are not to be construed as limiting same.

DETAILED DESCRIPTION OF THE PREFERRED AND ALTERNATIVE EMBODIMENTS

For a general understanding of the features of the invention, the preferred embodiment is shown in FIGS. 1-4 of the drawings. In the drawings, like reference numerals have been used throughout to designate identical elements.

Figure 1:
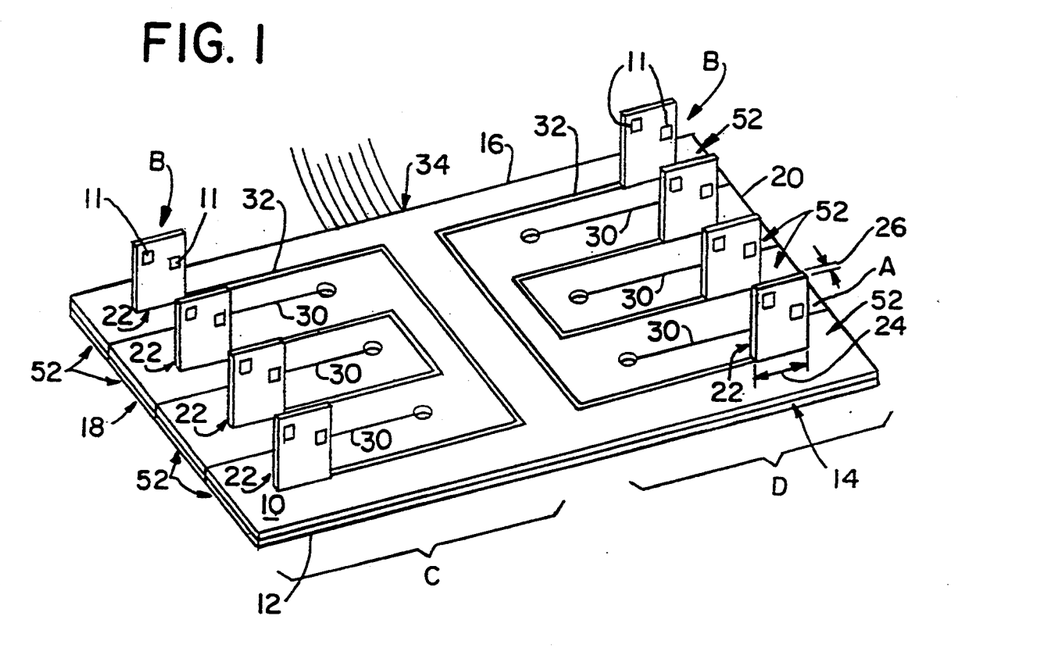
FIG. 1 is a perspective view of a cylindrical cuff with frayed ends in accordance with the preferred embodiment of the present invention constrained to a generally flat, uncurled configuration.
Figure 2:
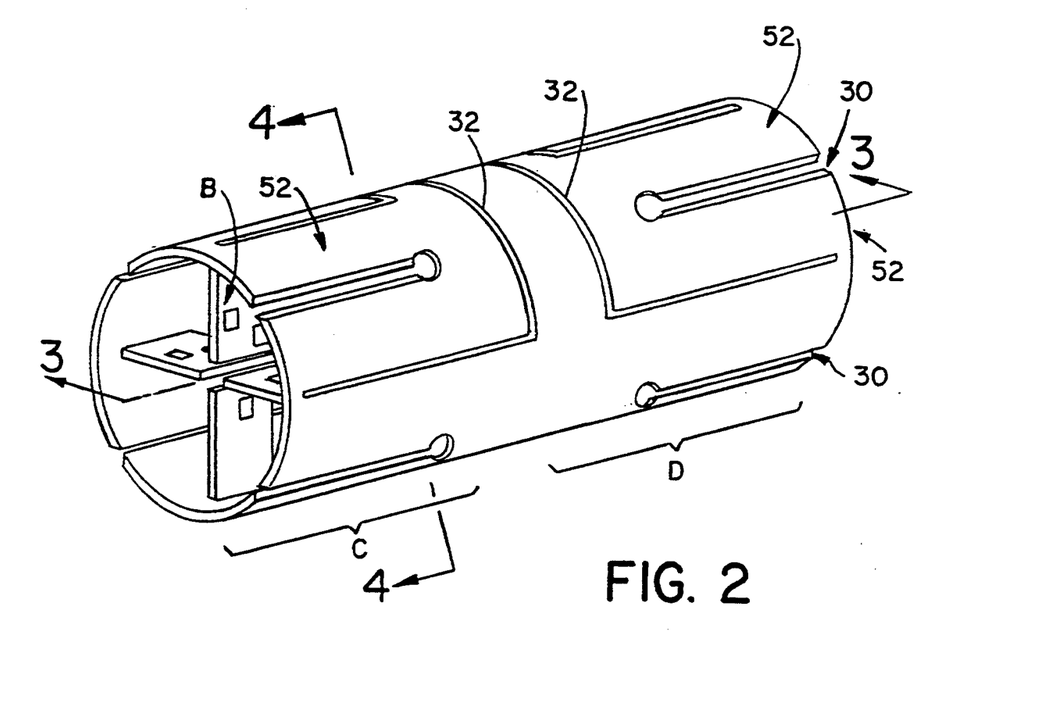
FIG. 2 is a perspective view of the cylindrical cuff of FIG. 1 in its curled and relaxed state.
Figure 3:
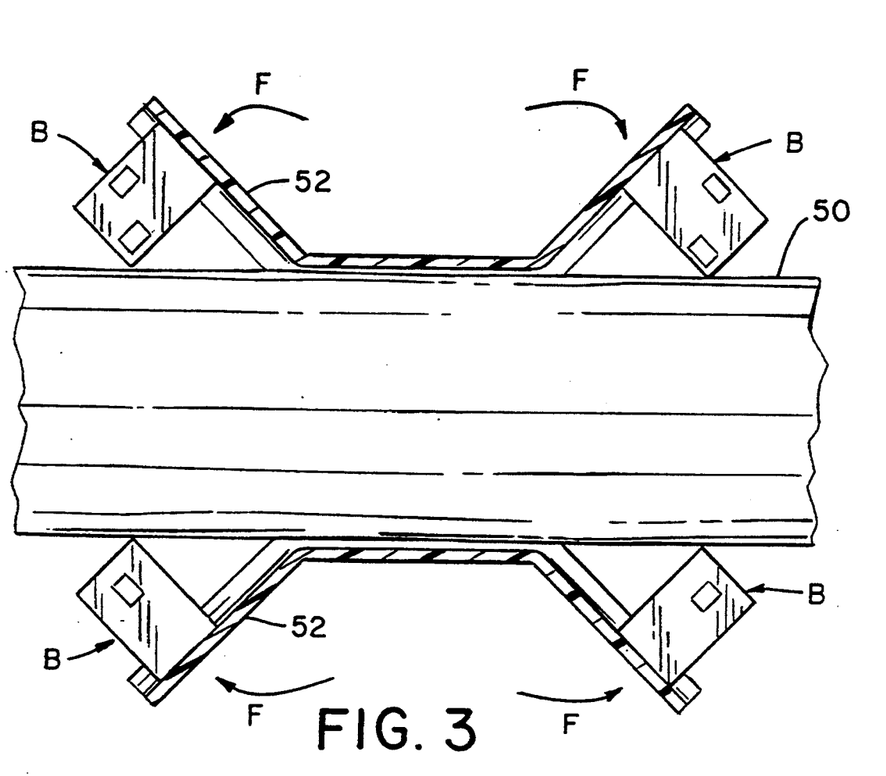
FIG. 3 is a sectional view of the cylindrical cuff of FIG. 2 taken along line 3—3, installed over a body tissue fiber in a semi-embedded condition.
Figures 5, 6:
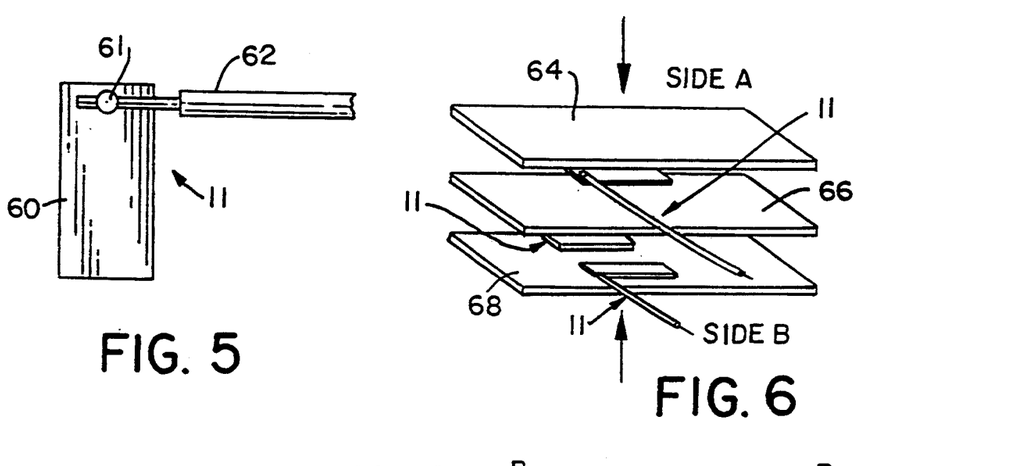
FIG. 5 is an elevational view of an electrically conductive electrode construction for use with the present invention.
FIG. 6 is an elevational view of a fin member construction for carrying one or more electrode constructions of FIG. 5.

With reference to FIGS. 1-3, an implantable cuff for encircling a nerve or other tissue includes a nonconductive resilient layer A to which one or more conductive segments B are attached or imbedded. For ease of discussion, each of the fin members as shown in FIG. 6 carrying electrodes 11, will be referred to as conductive segments B. Of course, as indicated above, the segments B may be electrically conductive or medication or otherwise fluid conductive. The layer A is illustrated in an opened or unrolled position for the sake of illustration but preferably comprises a short section of non-conductive cylindrical surgical tubing. The tubing is slitted once longitudinally over its length. The layer A is self-curling and is, therefore, self-biased to curl into its original cylindrical shape whereupon the first edge 14 abuts the second edge 16.

With continued reference to FIGS. 1-3 but with particular attention to FIG. 1, the layer A includes a first generally planar surface 10 and an oppositely disposed second generally planar surface 12. In the preferred embodiment, the layer A is generally rectangular and extends from a first edge 14 to an oppositely disposed second edge 16 and from a first or arresting end 18 to an oppositely disposed second or escape end 20.

A plurality of cutout regions 22 are disposed over the first and second generally planar surfaces 10, 12. Each of the cutout regions 22 has a longitudinal or first dimension 24 parallel to the first edge 14 which is initially slightly less than the width of the conductive segments B. The cutouts 22 further include a traverse or a second dimension 26 parallel to the first end 18 which is initially slightly less than the width of the conductive segments B. As illustrated in the Figures, each of the cutouts 22 have a conductive segment B received therein. Also, each of the conductive segments B is preferably provided with a plurality of electrodes 11 on first and second sides thereof.

In this preferred embodiment, the conductive segments B are electrically conductive. However, through simple modification of the structure of the electrodes 11, such as by forming fluid conduits or ducts, the elements are adaptable to become medication conductive. In addition, a selected one or more of the conductive segments may be adapted to be medication conductive while the other segments remain electrically conductive for a combined chemical and electrical stimulation. Further, the chemical and electrical conduction is not constrained to flow only into the nerve from the cuff. Rather, the chemical and electrical conductive elements conduct chemicals and electricity both from the cuff to the nerve and into the cuff from the nerve for stimulating and monitoring various nerve properties, activities, and characteristics, respectively. The fabrication of an electrically conductive segment B into a fin member will be described in greater detail below.

In the preferred embodiment illustrated in FIGS. 1-4, a plurality of circumferentially separated longitudinal slices 30 are made into the self-curling sheet A. Each of these longitudinal slices are made completely through the sheet A substantially equidistant between the conductive segments B. A first set of the longitudinal slices are made in parallel at the first end C of the sheet A, while a second set of slices are made in parallel at the second end D of the sheet A. In this manner, both ends of the implantable nerve cuff appear "frayed" after the cuff is permitted to relax and return to its original cylindrical tube shape. This is best seen in FIG. 2 wherein the implantable cuff is illustrated in its curled and relaxed cylindrical state.

With reference to FIGS. 1 and 2, each of the plurality of conductive segments B are provided with two electrodes 11 on a first side and a single electrode (not shown) on a second side. These electrodes are individually connected to an operatively associated electrical power source through individual fine conductive wires. In the Figures, the fine conductive wires are illustrated as bundles of conductors 32 which extend longitudinally from the conductive segments B to a location between the first end C and the second end D of the implantable cuff. From that point, the plurality of bundles 32 extend circumferentially around the implantable cuff to a common exit area 34. There, the plurality of bundles of conductors 32 extend axially away from the nerve encircled by the implantable cuff for subsequent attachment to the operatively associated source of electrical power.

In the preferred embodiment, the plurality of bundles of conductors 32 extend from the conductive segments B between first and second layers 40, 42 comprising the non-conductive sheet A. The first layer 40 is preferably a portion of a cylindrical surgical tube. The second layer 42 is a single layer of silastic coated with MDX adhered to the first layer 40 in a manner described more particularly below.

Although the preferred embodiment includes electrically conductive segments B having one or more electrodes on the front and back sides thereof, other constructions are possible. One such alternative includes forming a micro-multielectrode array in silicone using semiconductor fabrication technology. An example of this approach is Wim L. C. Rutten, Harmen J. Van Wier and Johan H. M. Put, "Sensitivity and Selectivity of Intraneural Stimulation Using a Silicon Electrode Array," *IEEE Trans. Biomed. Eng.*, vol. 38, pp. 192-198, February 1991. Using this and similar technologies currently available including micro-lithography and micro-integrated electronics, the conductor bundles 32 are formed on fine silicon substrates. In this way active electronics are included on the cuff itself.

In use, the implantable cuff is manually unrolled and maintained in the position illustrated in FIG. 1. Next, the unrolled implantable cuff is aligned with and positioned over the target nerve 50. The cuff is then permitted to re-curl into its original tubular shape around the nerve. A suture is installed to hold the central region of the cuff tight against the nerve. Initially, each of the plurality of spring members 52 formed by the plurality of longitudinal slices 30 assume a position illustrated in FIG. 3. As described above, the plurality of spring members 52 are made of the same materials comprising the implantable cuff and, therefore, are self-biased to "flatten" or assume their natural, relaxed and cylindrical profile illustrated in FIG. 2. This being the case, each of the plurality of conductive segments B or fin members, carried on the plurality of spring members 52 experiences a force F tending to slowly urge the plurality of conductive segments B radially into the nerve itself. The forces F are spring constants of the material and are therefore selectable through the proper choice of the materials comprising the self-curling non-conductive sheet A. Also, the size and orientations of the plurality of longitudinal slices 30 and corresponding spring members 52 formed thereby play a role in the forces F.

Figure 4:
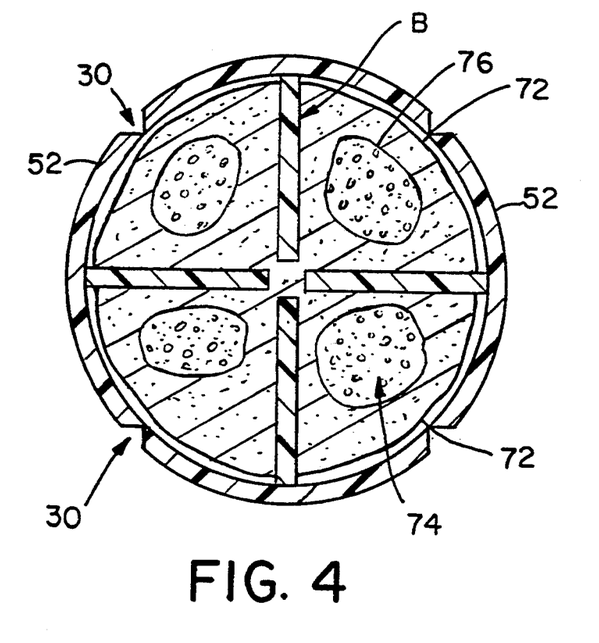
FIG. 4 is a sectional end view of the cuff in the curled frayed end configuration of FIG. 2 taken along line 4—4 and disposed around a body tissue fiber in its final relaxed state.

FIG. 4 illustrates the cylindrical nerve cuff electrode of the preferred embodiment in its final relaxed state as shown in FIG. 2, applied on a nerve. In general, a nerve 70 is surrounded by a loose membrane called epineurium 72. The nerve is typically organized into several groups of axons called fascicles 74. Each fascicle 74 is surrounded by a membrane called perineurium 76. In use, the cylindrical nerve cuff electrode of the present invention slowly inserts the conductive members B through the epineurium 72 and into the nerve 70 without puncturing the perineurium 76 of any of the fascicles 74 within the nerve. Instead, the fascicles 74 are displaced, rather than pierced. The method of using the preferred embodiment inserts electrodes into the nerve interfascicularly without penetration of the perineurium. The conductive segments are somewhat flexible to better penetrate the nerve without puncturing the perineurium. The electrodes are gently and slowly migrated into the nerve gradually over a period long enough to minimize the pressure on the nerve. Typically, the time period required for the cuff to function properly extends from about one (1) hour to several days for various applications and situations. The driving force which motivates the conductive members B inward is provided by the mechanical action of the spring members 52. This unique design illustrated in the Figures allows the placement of the electrodes deep inside the nerves with minimal damage to the nerve itself. The electrodes are each capable of activating separate and distinct regions within the nerve, along the longitudinal and radial axis of the nerve, which was not previously accessible by other types of electrodes without associated damage. The electrodes are also capable of sensing small neural signals with better signal to noise ratios due to the close proximity of each the electrodes to the axons comprising the fascicles.

Another version of the preferred embodiment illustrated in FIGS. 1-4 includes one or more of the conductive segments B connected to an end of a beam of resilient non-conductive material. The beam is constructed simply by extending the longitudinal slices 30 entirely through the sheet of opened tubing, joining at the middle. In the constructions shown in FIGS. 1-4, four (4) such beams would thus be created. The beam once cut from the tube, is aligned longitudinally along the direction of the nerve or other body tissue with the fin member(s) positioned on the beam ends and facing the nerve. Next, a suture is installed over the beam midpoint and nerve, tying the two together. The suture is tightened, transforming the originally flat beam into a resiliently biased curved spring. The fin members on the springs are drivingly urged into the nerve or other body tissues as the spring straightens, relaxing to its original shape.

With reference now to FIGS. 5-10, the fabrication of the preferred radially penetrating intrafascicular nerve cuff electrode will be explained. First, with reference to FIG. 5, an electrode 11 is preferably formed by spot-welding a 7-strand stainless steel teflon coated wire 62 to a platinum foil electrode 60 at a weld point 61. However, as indicated above, silicon thin-film technology provides a ready alternative to the welded stainless steel approach.

In the preferred embodiment, three electrodes 11 formed in the manner set forth above are provided in conjunction with three silastic sheets. A first sheet 64 forms a first or front side of the conductive segment B. A second intermediate sheet 66 electrically isolates the electrodes while a third sheet 68 forms the second or rear side of the conductive segment B. As illustrated in FIG. 6, the three silastic sheets 64, 66, and 68 are glued together with MDX 4-4210 elastomer and are then cured in an oven or press. Three electrodes 11 are interstitial deposited between the silastic sheets to form an electrode "sandwich."

Figure 7A:
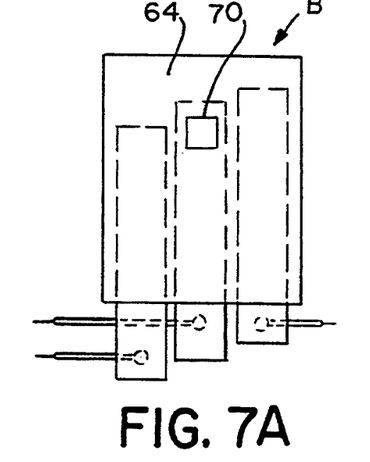
FIGS. 7a and 7b are, respectively, front and rear elevational views of the fin member construction of FIG. 6 carrying three electrodes of FIG. 5.
Figure 7B:
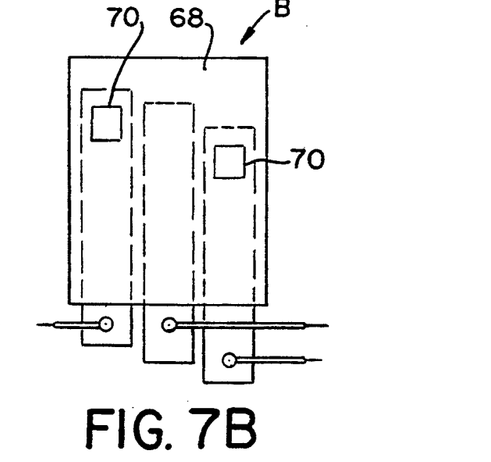

Next, with reference to FIGS. 7a and 7b, the conductive segments B are trimmed into a preselected configuration which, in the preferred embodiment, is generally rectangular in shape. Other shapes or profiles, however, are possible. The first or front side of the conductive segment B comprising the first sheet 64 is trimmed forming a first window 70 exposing a first electrode therethrough. Similarly, with reference to FIG. 7b, the second or rear side of the conductive segment B comprising the third sheet 68 is trimmed forming windows 70 exposing a second pair of electrodes. In this manner, the conductive segment B includes a single electrode on its front side while having a pair of electrodes on the rear side. Obviously, other combinations including more or less electrodes or other fluid communicating apparatus are possible or combinations thereof. That is, fluid conduits may be substituted for the electrodes whereby medications or other chemicals may be administered to, or sampled from, the target nerve or body tissue.

Figure 8:
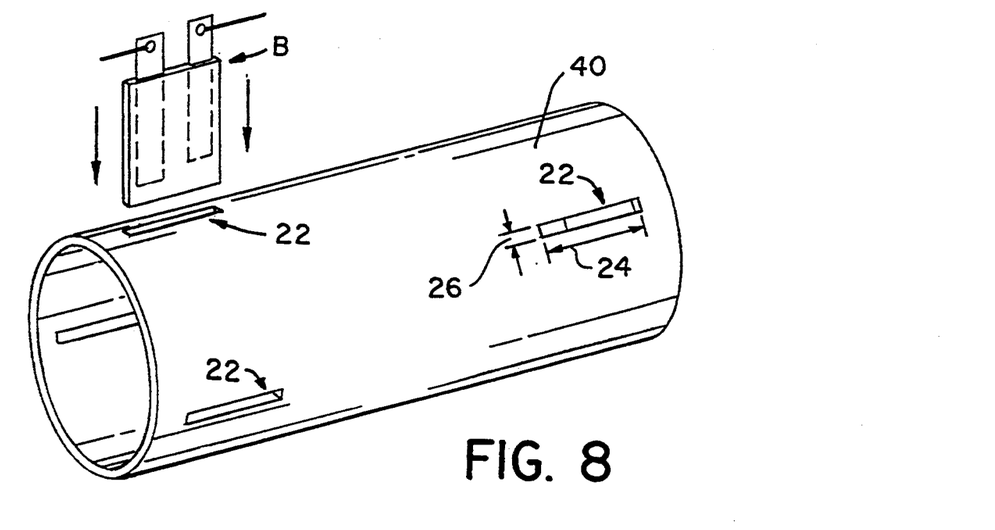
FIG. 8 is an elevational view of the fabrication step of inserting a fin member construction of FIG. 6 into a surgical tube section.

FIG. 8 illustrates the step of inserting a typical conductive segment B into the surgical non-conductive cylindrical tubing forming the first layer 40 of the implantable cuff of the preferred embodiment. As particularly illustrated in FIG. 1 above, the preferred embodiment includes eight conductive segments B. Accordingly, the surgical tubing is sliced in eight longitudinally-extending locations forming the cut-out portions 22 described above. Eight individual conductive segments B are inserted into the eight cut-out portions 22. The segments are fictionally held in place since the longitudinal and traverse dimensions 22, 26 of the cut out regions 22 are slightly less than the size of the inserted segments B. The 7-strand stainless steel teflon coated wires (not illustrated) are bundled together after all eight conductive segments B are inserted into the surgical tubing.

Figure 9:
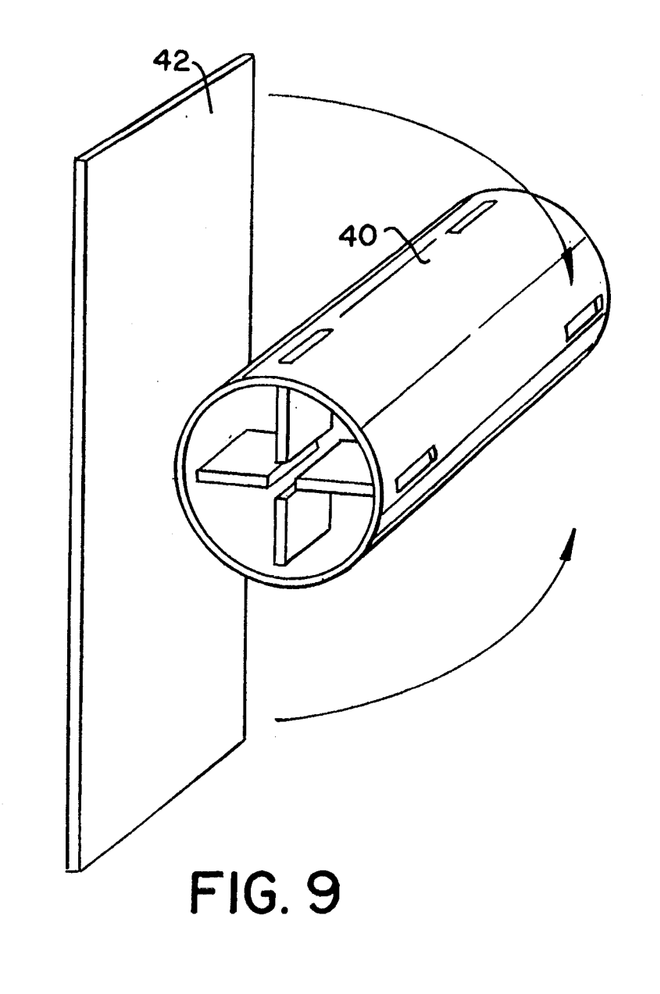
FIG. 9 is an elevational view of the fabrication step of wrapping a silastic sheet around the construction of FIG. 8.
Figure 10:
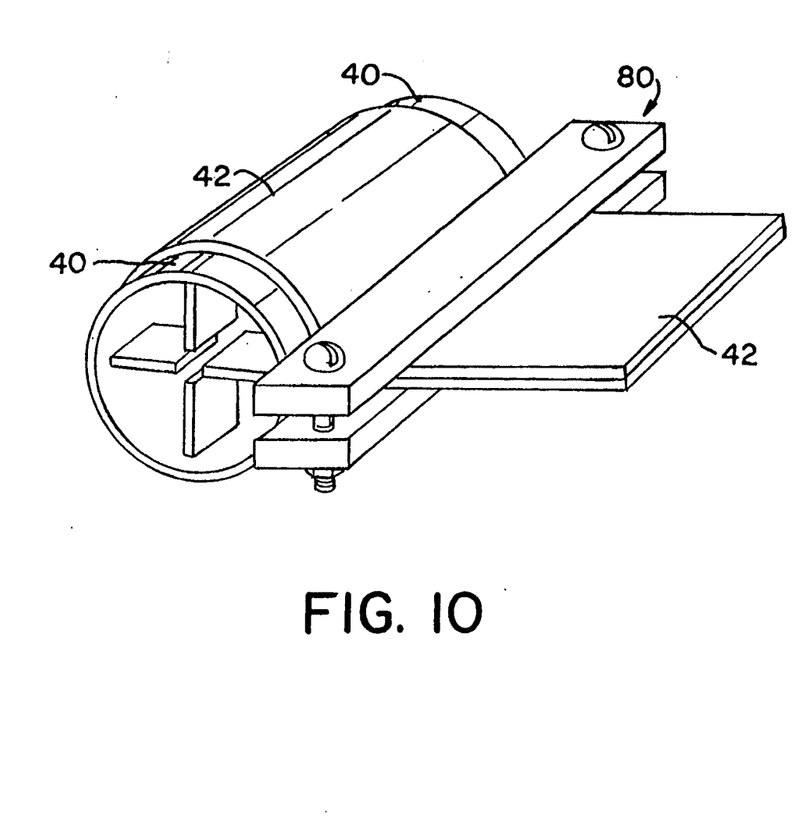
FIG. 10 is an elevational view of the fabrication step of clamping and curing the construction of FIG. 9.

Next, with reference to FIGS. 9 and 10, a second layer 42 of silastic coated with MDX is wrapped once around the surgical tubing comprising the first layer 40 with the conductive segments B inserted therein. The second layer 42 is clamped in place using a suitable clamping mechanism illustrated generally as a simple pinned block 80. In the preferred embodiment, the second layer 42 encapsulates the bundled teflon coated wire extending from the plurality of electrodes attached to the conductive segments B. In this manner, the fine wire is protected from possible damage in handling or the like.

Lastly, with reference to FIG. 10, the implantable cuff is cured whereupon the clamp 80 is cut off along with the extra portions of the second layer 42. A longitudinal slit (not shown) is cut into the cuff through both the first layer 40 and the second layer 42 for its entire length. Also, the plurality of longitudinal slices 30 are suitably established at this time.

Figure 11:
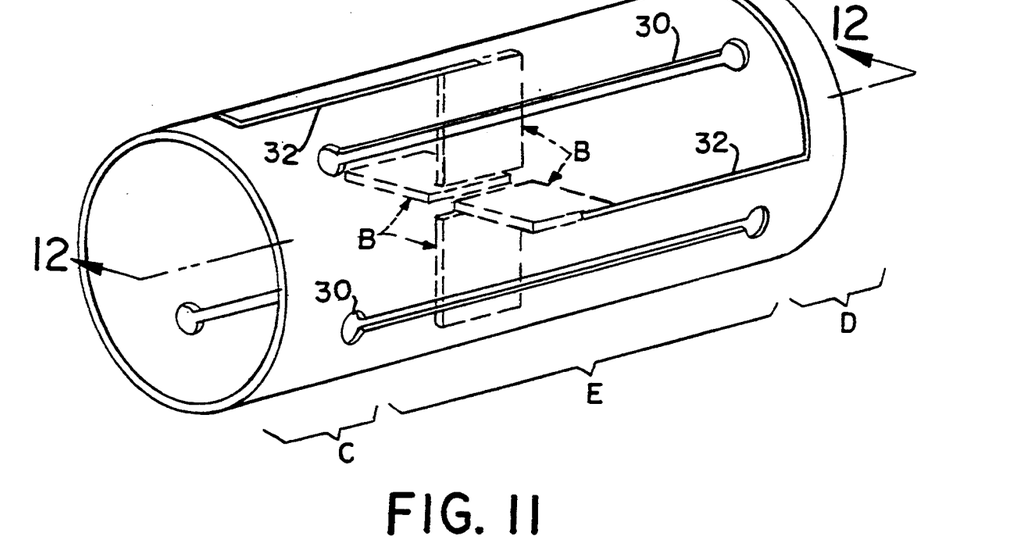
FIG. 11 is a perspective view of a cylindrical cuff in accordance with another embodiment of the present invention in a curled and relaxed configuration.
Figure 12:
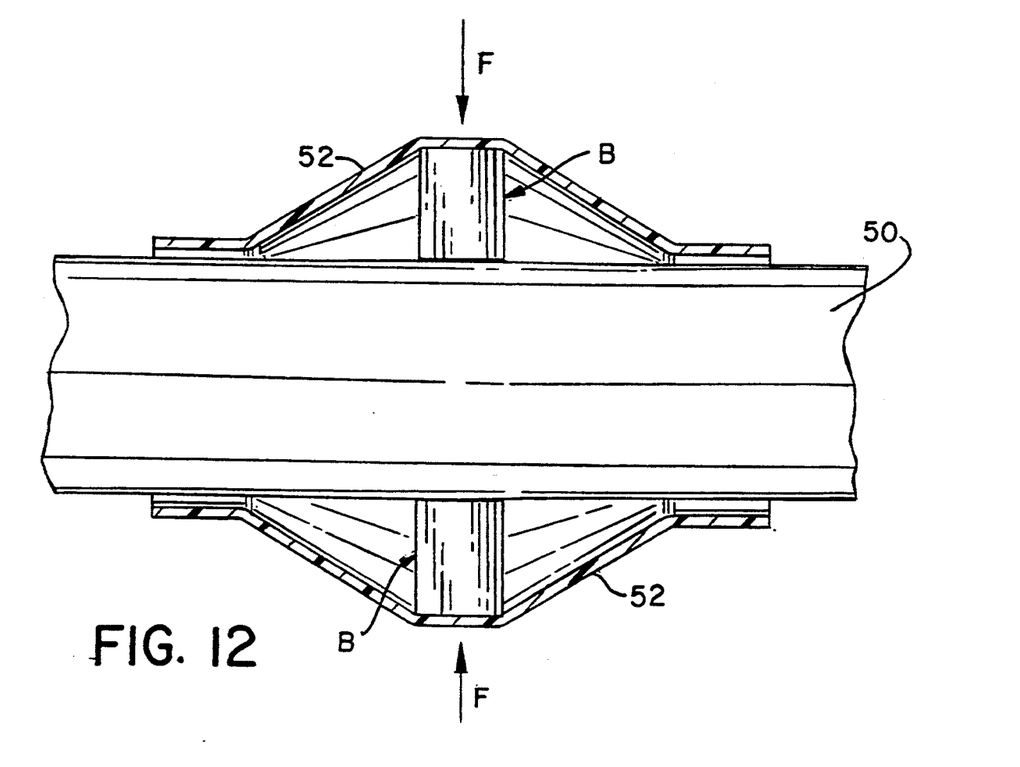
FIG. 12 is a sectional view of the cylindrical cuff of FIG. 11 taken long line 12—12 and installed over a body tissue fiber in a semi-embedded condition.

Next, with reference to FIGS. 11 and 12, a second embodiment of the nerve cuff electrode will be described. In this embodiment, the plurality of longitudinal slices 30 are made near the center E of the elongate cylindrical cuff, rather than the extreme ends C and D. That is, in the second embodiment, the ends are not frayed, but rather, the ends are substantially circumferentially contiguous around the target nerve or body tissue.

In use, the alternative embodiment implantable cuff is manually unrolled and maintained in the position illustrated in FIG. 1. Next, the unrolled implantable cuff is aligned with and positioned over the target nerve 50. Initially, each of the plurality of spring members 52 formed by the plurality of longitudinal slices 30 assume a position illustrated in FIG. 12. As described above, the plurality of spring members 52 are made of the same materials comprising the implantable cuff and, therefore, are self-biased to "flatten" or assume their natural, relaxed and cylindrical profile illustrated in FIG. 11. This being the case, each of the plurality of conductive segments B, carried on the plurality of spring members 52 experiences a force F tending to urge the plurality of conductive segments B radially into the nerve itself. The forces F are spring constants of the material and are therefore selectable through the proper choice of the materials comprising the self-curling non-conductive sheet A. Also, the size and orientations of the plurality of longitudinal slices 30 and corresponding spring members 52 formed thereby play a role in the forces F. In this embodiment, the cuff tends to grow or lengthen as the spring members 52 relax, slowly radially urging the conductive members B into the nerve or other body tissue. FIG. 4 illustrates the cylindrical nerve cuff electrode of the alternative embodiment in its final relaxed state as shown in FIG. 11, applied on a nerve.

Figure 13:
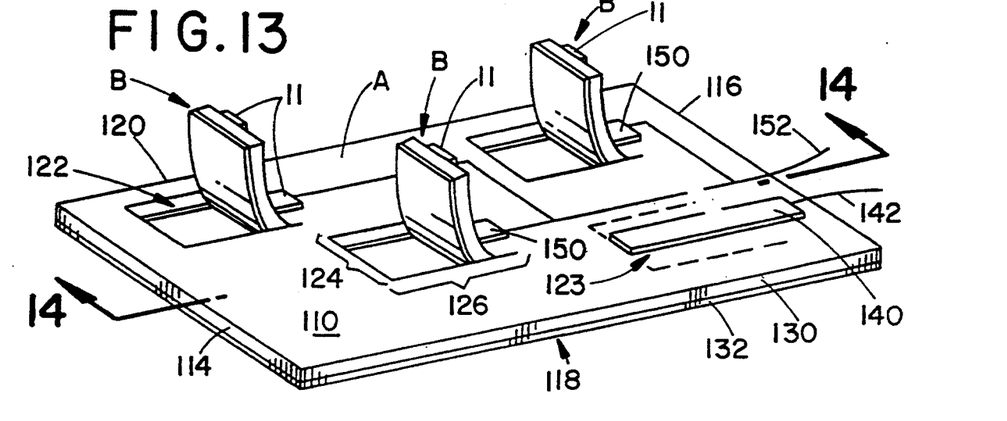
FIG. 13 is a perspective view of a self-curling spiral cuff in accordance with another embodiment of the present invention constrained to a generally flat, uncurled configuration.
Figure 14:
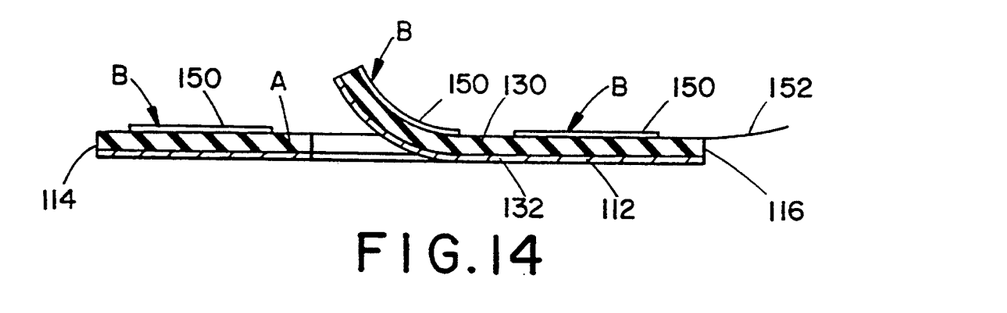
FIG. 14 is a sectional view through section 14—14 of FIG. 13.
Figure 15:
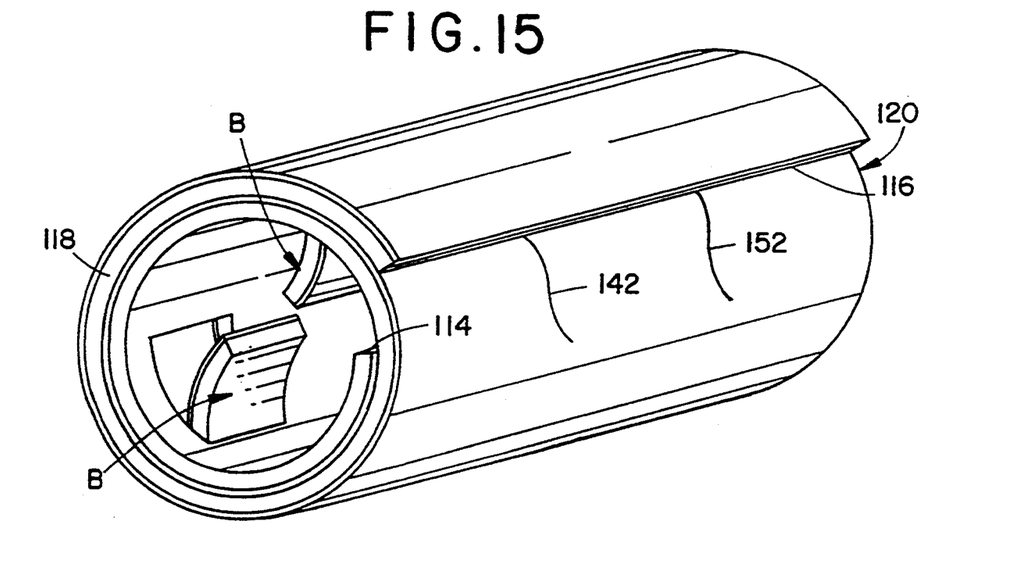
FIG. 15 is a perspective view of the cuff of FIG. 13 in a curled configuration.
Figure 17:
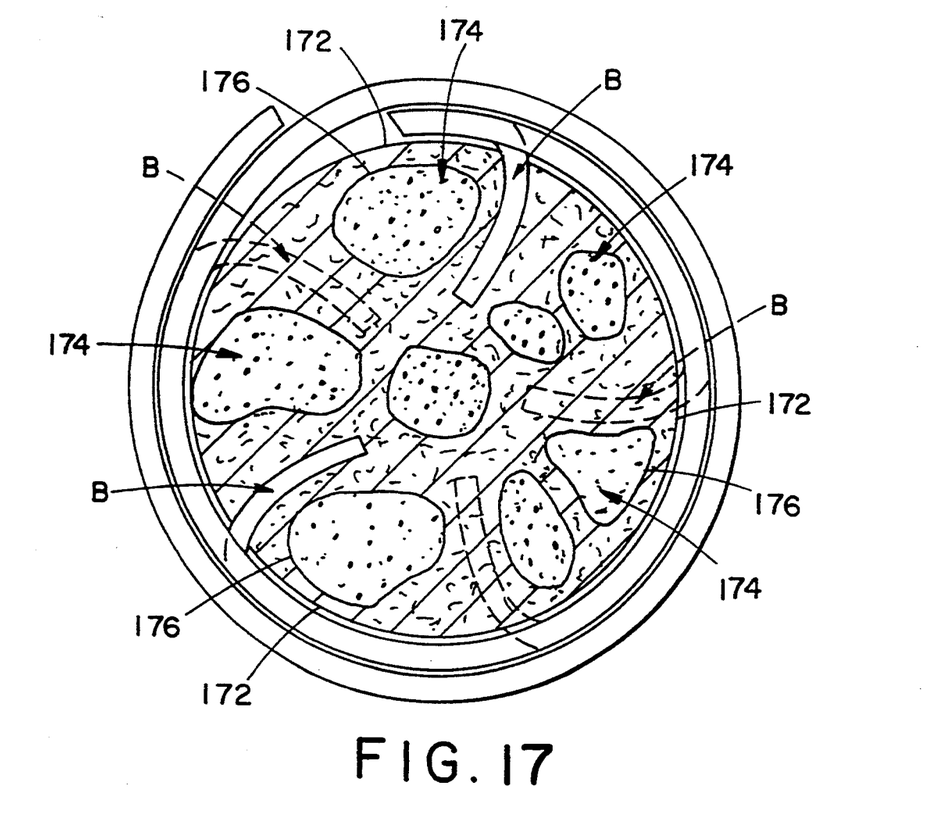
FIG. 17 is a general sectional view of the cuff in the curled configuration of FIG. 15 disposed around a body tissue fiber; and, FIG. 18 is an elevational view of a self-curling cuff in accordance with an alternative electrode configuration and pattern.

With reference now to FIGS. 13 and 14, another alternative embodiment of the implantable cuff includes a self-curling non-conductive sheet A to which one or more conductive segments B are attached or embedded. The self-curling sheet is self-biased to curl into a tubular spiral or roll as illustrated in FIGS. 15 and 17.

Referring again to FIGS. 13 and 14, the self-curling sheet A includes a first generally planar surface 110 and an oppositely disposed second generally planar surface 112. In the preferred embodiment, the self-curling sheet is generally rectangular and extends from a first edge 114 to an oppositely disposed second edge 116 and from a first or arresting end 118 to an oppositely disposed second or escape end 120. A plurality of cutout regions 122 are disposed over the first generally planar surface 110 and correspondingly over the oppositely disposed second generally planar surface 112. Each of the cutout regions 122 has a longitudinal or first dimension or surface 124 parallel to the first edge 114 which is slightly greater than the width of the electrodes 11 formed on the conductive segments B. The cutouts 122 further include a traverse or a second dimension or surface 126 parallel to the first end 118 which is slightly less than the length of the electrodes 11 formed on the conductive segments B. As illustrated in the Figure, none of the cutouts 122 completely remove or sever portions of the self-curling sheet A, but rather, form flaps or finger portions. Each of the flaps have at least one conductive segment in the form of an electrode 11 disposed thereover. In this manner, a conductive electrode pad is formed merely by folding the flaps upwardly as illustrated in the Figure. The conductive segments B thus carry the electrodes 11 thereon.

In the alternative embodiment illustrated, the conductive elements are electrically conductive. However, through simple modification of the structure of the segments B, such as by forming the electrodes 11 into fluid conduits, the elements become medication conductive. In addition, a selected one or more of the conductive segments may be adapted to be medication conductive while the other segments remain electrically conductive for a combined chemical and electrical stimulation. Further, the chemical and electrical conduction is not constrained to flow only into the nerve from the cuff. Rather, the chemical and electrical conductive elements conduct chemicals and electricity both from the cuff and into the cuff for monitoring various nerve properties, activities and characteristics.

Figure 18:
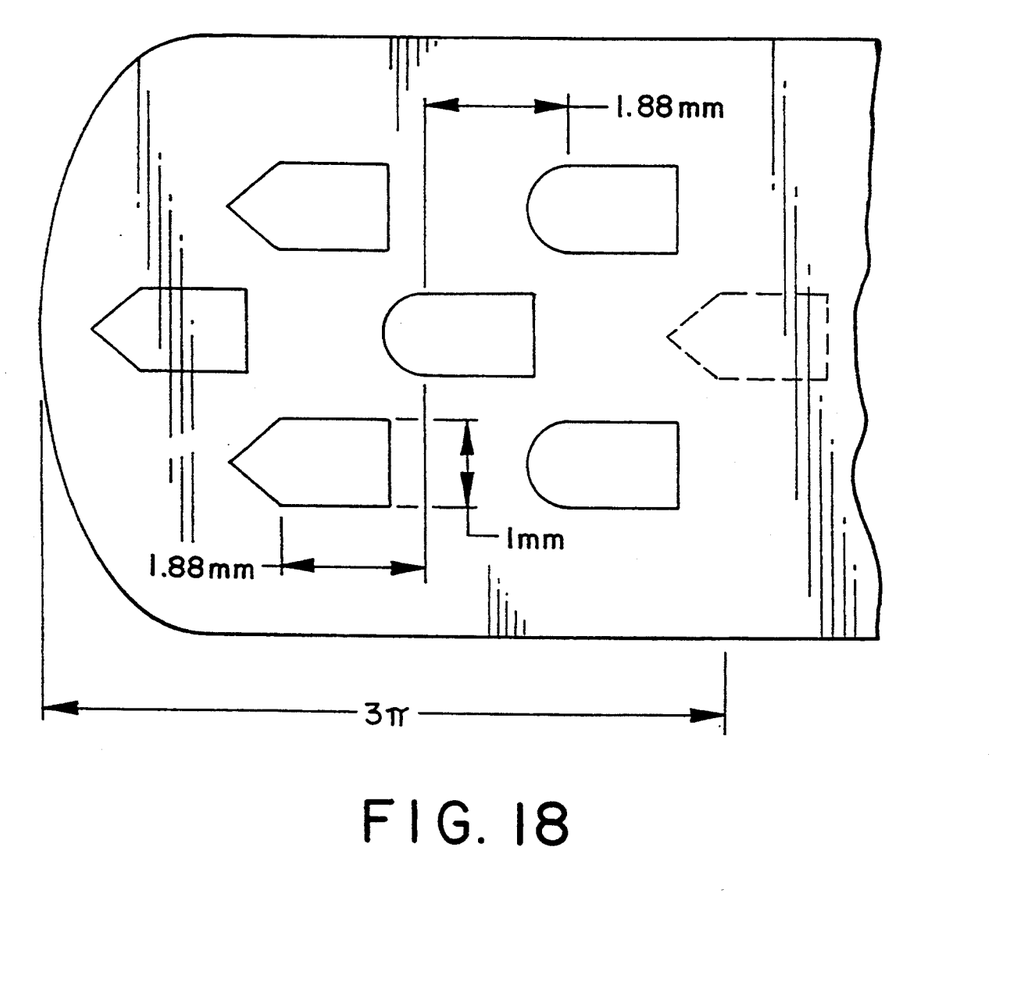

As illustrated in FIG. 13, three flaps or fingers comprising the conductive segments B are upwardly bent. A fourth cutout 123 is illustrated by a dashed line on the first generally planar surface 110. The dashed line marks the locations of the longitudinal or first dimension or surface 124 parallel to the first edge and the traverse or second dimension or surface 126 parallel to the first end. As illustrated, three basic cuts through the self-curling non-conductive sheet A leave a fourth edge comprising a hinge portion for the resulting flap. In the alternative embodiment illustrated, each of the flap or finger portions are rectangular but may be substituted with triangular or semicircular-tipped flaps as shown in FIG. 18.

In the preferred embodiment illustrated in the Figures, the self-curling sheet is self-biased to curl by a first layer 130 and a second layer 132 of dissimilar size. The first layer 130 is an elastomeric material which is stretched traversely between first and second edges 114 and 116 before it is laminated to the second layer 132. When the first layer is relaxed, it tries to contract but the second layer holds the adjoining surface stretched. More particularly, the first surface 110 contracts smaller than the second surface 112 causing the sheet A to curl. In the preferred embodiment, the first and second layers are both curled silicone rubbers adhered together by an adhesive layer, such as silicone rubber, epoxy, or the like. The layers are assembled uncured and later air cured, temperature cured, vulcanized, or the like after fabrication.

Other biocompatible materials are contemplated. For example, the stretchable first sheet 130 may be cured silicone rubber and the second sheet 132 may be Teflon film, a platinum mesh, or other biocompatible sheet. As yet another alternative, the stretched first layer may also be a non-rubber polymeric material which is both biocompatible and exhibits appropriate elastomeric properties. It is to be appreciated, that in the Figures, the thicknesses of the sheets are exaggerated for simplicity of illustration.

The electrodes 11 are disposed in, on, or below the first sheet 130. The conductive segments include a first segment 140 extending traversely, i.e., parallel to the first end 118. As illustrated in FIG. 13, the first segment 140 rests on a flap or finger portion which is not yet bent upwardly as are the other flaps or finger portions in the figure. The first electrode 140 has a width commensurate with the desired electrode and has a length commensurate with the size of the radius of the target nerve as will be discussed in greater detail below. Each of the electrodes extend radially inwardly in the curled configuration illustrated in FIG. 15. In preferred usage, the electrode 140 functions as a cathode on the surface of the nerve bundle. A conductive lead 142 extends from the electrode portion to the second edge 116 for interconnection with an appropriate source of electrical potential. The lead may be welded to the electrode, integral with the electrode, or the like.

A plurality of second segments or electrodes 150 are disposed over the cutout areas 122. As illustrated, the second segments or electrodes 150 may be electrically interconnected in a variety of configurations including arrangements for bipolar and/or tripolar stimulation. A conductive lead bundle 152 extends to the second edge for connection with other lead wires and/or to an appropriate source of electrical potential. Most commonly, the second electrodes 150 are connected to cooperatively function as a cathode/anode pairs for bipolar or tripolar stimulation. However, alternative electrical connections are possible including, but not limited to, connection to separate and independent sources of electrical energy for each electrode in the cuff. Separate and distinct stimulation can be applied between each individual electrode with a preselected electrode acting as a reference or, separate and individual stimulation can be applied between any two selected pairs of electrodes. Similarly, chemical stimulation or collection is possible as described above merely by configuring the conductive members as fluid conduits. Arrangements of medication or chemical conductive members include single connection to separate and independent sources of the medication or chemicals or parallel connections between the fluid conductive members and a common source.

Figure 16:
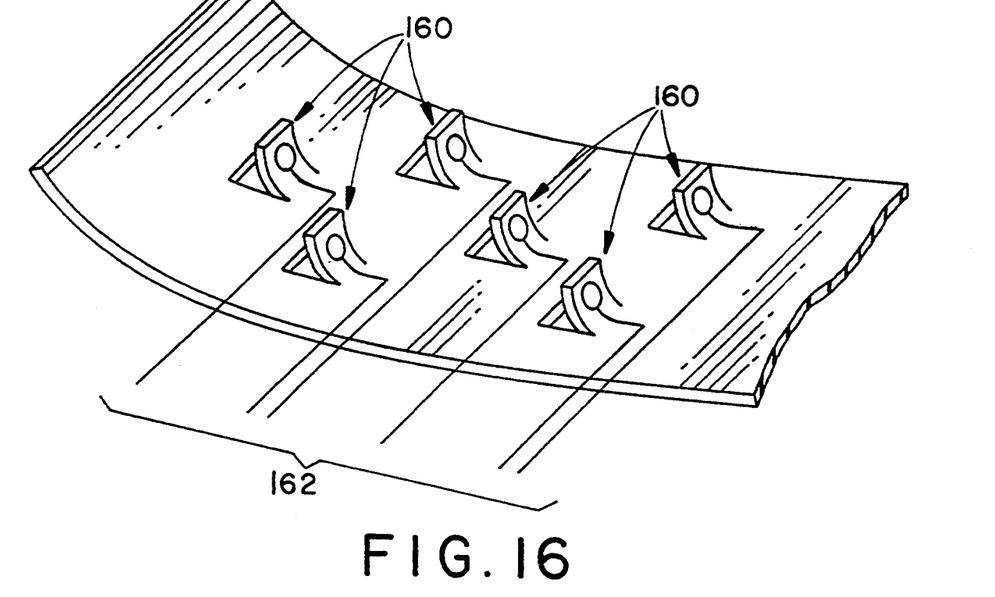
FIG. 16 is a perspective view of the self-curling cuff of FIG. 13 in a semi-uncurled configuration.

In the embodiment illustrated in FIG. 16, each of the individual electrodes 160 have separate conductive leads 162 connected thereto for specialized electrical stimulation according to a desired treatment.

As an alternative embodiment to that of FIG. 16, selected ones or all of the conductive members, illustrated as electrically conductive, may be medication or chemically conductive to draw or add chemicals from or to the nerve. As illustrated, separate control over each chemically conductive member is possible using chemically conductive leads 162.

The electrically or chemically conductive regions are relatively thin. Ideally, the conductive regions are the thinnest layer which still conducts the amount of electricity or chemicals required to be conducted by the electrodes. The conductive region may be a conductive polymer, a conductive paint, a very thin layer of metal, or thin wires. The thin metal layer may be vacuum deposited, sputtered, a thin or ultra-thin foil, or the like. The electrically conductive layers are also biocompatible such as platinum, gold, iridium, stainless steel or the like.

Looking to specific details of an exemplary method of cuff manufacture for this embodiment, a sheet of cured silicone elastomer 130 which has a thickness of 0.005 inches is fixed at opposite ends by clamps. In the preferred embodiment, silastic is used for both sheets. Sheets of other type or thickness can also be used. The sheet is then stretched over a steel or otherwise rigid frame. The length of the exposed sheeting between the clamps in the unstretched state if varied according to the final diameter of the desired cuff. A shorter length of unstretched sheeting results in a greater amount of stretch and a smaller final cuff diameter.

The next step is to place the conducting material, e.g., platinum foil 0.001 inches thick, over the stretched sheet. Gold, conductive polymers or other biocompatible conductors may also be used. The stimulating portion of the conductive segments 140, 150 is only that region exposed through windows described in greater detail below. The platinum foil segments are connected to the stimulator via electrical conductors, e.g., metals and conducting polymers 142, 152 which are spot-welded or otherwise connected to the platinum. Alternately, the platinum foil which forms the electrodes can extend integrally the entire length of the cuff. The foil or wire extends lengthwise down the cuff to the end and is later connected to lead wires from the stimulator by spot-welding or soldering. Epoxy or silicone rubber is used to insulate the exposed metal. Alternately, cuffs and lead wires may be connected and formed in a single step prior to mounting on the cuff.

After the conducting surfaces 140, 150 have been positioned, a thin layer of uncured silicone elastomer or adhesive is spread over the entire surface of the stretched sheet and the metal foil lying on top of it. The second silicone elastomer sheet 132 is then carefully placed on top of this. Next, the segment windows are cut out, exposing the stimulating portion of the conductive segments 140, 150. A pair of steel plates are next placed over the entire configuration and clamped down with screws or other fastening mechanisms. Shim stock is used to obtain an overall thickness of the cuff of about 0.011 inches. The assembly is placed in an oven and heated for about 30 minutes to allow the silicone elastomer to fully cure. After cooling, the cuff is removed and the edge is trimmed to the proper dimensions determined for the specific application. Next, the cutout regions are stamped, punched or otherwise effected. The tabs or finger portions comprising the conductive segments B are upwardly bent into an orientation approximately perpendicular with the surface of the cuff. The resultant cuff curls naturally wherein the tabs or finger portions extend radially inwardly.

The predominant curling characteristic of the cuff illustrated in its curled state in FIG. 15 is achieved by stretching the first sheet as described above. The stiffness of the metal within the cuff allows some plastic deformation by hand which is used to maintain the conductive segments B in the position perpendicular with the inner surface of the cuff. That is, substantially inwardly radially extending. The diameter of the curl can typically be altered by hand through plastic deformation of the metal within the cuff to about 10–15%. Once the cuff has been implanted, small amounts of swelling of the tissue within the cuff are accommodated through the cuff's ability to flex or open large enough to be greater than the largest expected swollen nerve outer diameter. This reduces the risk of tissue trauma. The cuff thus has the advantage that slight variations of the tissue will be automatically accounted for by the interstitial gap between the cuff and the nerve, reducing the risk of danger to the nerve.

An example of the specific dimensions which produce a suitable cuff will now be described. A sheet of cured silicone elastomer, 13 centimeters long, is stretched to a length of about 15 centimeters. The uncured adhesive layer is next applied and a second cured sheet of silastic, 15 centimeters long, is placed on top of it. The cured sheets are both 0.005 inches thick. The total thickness of the cuff is 0.011 inches as it is compressed between the two steel plates with appropriate shim stock placed between the plates. After curing, the cuff is removed and trimmed. A typical internal cuff diameter is approximately 3 mm and the circumference is approximately 103 mm. The diameter of the cuff can be varied by manual manipulation from 0.150 inches to 0.180 inches to adjust it to a particular nerve. The spacings between the rows of tabs or finger portions is 1.88 mm. Each of the tab or finger portions comprising the electrodes are 1 mm wide.

FIG. 17 illustrates the spiral nerve cuff electrode of the present invention in its contracted state as shown in FIG. 3, applied on a nerve. In general, a nerve 170 is surrounded by a loose membrane called epineurium 172. The nerve is typically organized into several groups of axons called fascicles 174. Each fascicle 174 is surrounded by a membrane called perineurium 176. In use, the spiral nerve cuff electrode of the present invention slowly inserts the conductive members B through the epineurium 172 and into the nerve 170 without puncturing the perineurium 176 of any of the fascicles 174 within the nerve. Instead, the fascicles 174 are displaced, rather than pierced. The method of using the preferred embodiment inserts electrodes into the nerve interfascicularly without penetration of the perineurium. The electrodes are gently and slowly migrated into the nerve gradually over several days in order to minimize the pressure on the nerve. The driving force F which motivates the conductive members B inward is provided by the mechanical coiling action of the spiral design. This unique design illustrated in the Figures allows the placement of the electrodes deep inside the nerves with minimal damage to the nerve itself. The electrodes are each capable of activating separate and distinct regions within the nerve, along the longitudinal and radial axis of the nerve, which was not previously accessible by other types of electrodes without damage. The electrodes are capable of sensing small neural signals with better signal to noise ratios due to the close proximity of each the electrodes to the axons comprising the fascicles.

Although the structure of the nerve cuff has been described using the Figure above, an important factor to the efficacy of such approach is the time dimension. That is, the conductive members need not be inserted radially into the nerve in a plane substantially perpendicular to the longitudinal axis of the nerve, but may also be inserted radially in a plane oblige to the longitudinal axis of the nerve so long as the rate of insertion is held in check such that the fascicles are displaced rather than pierced or otherwise damaged.

The invention has been described with reference to the preferred embodiments. Obviously, modifications and alterations will occur to others upon reading and understanding the preceding detailed description of the preferred embodiments. It is intended that the invention be construed as including all such alterations and modifications insofar as they come within the scope of the appended claims or the equivalents thereof.

Having thus described the preferred embodiments of the invention, the invention is now claimed to be:

1. A method of inserting a first member into an elongate nerve encased in an epineurium membrane and including at least one longitudinally extending group of axons surrounded by a perineurium membrane forming a fascicle, the method comprising the steps of:
   piercing said epineurium membrane with said first member; and,
   gradually radially urging said first member through said epineurium membrane and into said nerve avoiding said perineurium membrane over a predefined time period.

2. The method according to claim 1 wherein said radially urging step includes gradually radially urging said first member through said epineurium membrane and into said nerve avoiding said perineurium membrane over said predefined time period lasting long enough to avoid damage to said nerve.

3. A method of inserting a first member into an elongate nerve encased in an epineurium membrane and including at least one longitudinally extending group of axons surrounded by a perineurium membrane forming a fascicle, the method comprising the steps of:
   piercing said epineurium membrane with a first portion of said first member, the first portion being adapted for blunt piercing; and,
   radially urging said member through said epineurium membrane and into said nerve avoiding said perineurium membrane.

4. The method according to claim 3 further comprising:
   piercing said epineurium membrane with a second member connected to the first member, a first portion of the second member being adapted for piercing;
   urging said first member through said epineurium membrane and into said nerve avoiding said perineurium membrane; and,
   urging said second member through said epineurium membrane and into said nerve avoiding said perineurium membrane.

5. The method according to claim 4 wherein said first member epineurium piercing step and said second member epineurium piercing step are substantially simultaneously performed.

6. The method according to claim 4 wherein said first member urging step and said second member urging step are substantially simultaneously performed.

7. The method according to claim 6 wherein said first and second member urging steps include gradually urging said first portions of said first and second members through said epineurium membrane and into said nerve avoiding said perineurium membrane over a predefined time period.

8. The method according to claim 7 wherein said first and second member urging steps include gradually urging said first portions of said first and second members through said epineurium membrane and into said nerve avoiding said perineurium membrane over said predefined time period lasting more than one hour.

9. For use with an elongate nerve having several groups of longitudinally extending fascicles, each group surrounded by a perineurium membrane, a method of nerve electrode insertion comprising the steps of:

radially inserting a first electrode into said nerve at a first longitudinal position; and, simultaneously applying a first force on said nerve at said first longitudinal position, the first force substantially opposing a force on said nerve generated by said radially inserting step.

10. The method according to claim 9 further comprising the step of radially inserting a second electrode into said nerve at a second longitudinal position.

11. The method according to claim 10 wherein said first electrode inserting step and said second electrode inserting step are simultaneously performed.

12. The method according to claim 10 further comprising the step of applying a second opposing force on said nerve at said second longitudinal position simultaneous with said second electrode inserting step.

13. The method according to claim 12 wherein said first electrode inserting step and said second electrode inserting step are simultaneously performed.

14. The method according to claim 13 wherein said first electrode inserting step, said second electrode inserting step, said first force applying step and said second force applying step are all simultaneously performed.

15. The method according to claim 14 wherein:
said first electrode inserting step includes the step of inserting said first electrode between said nerve fascicles; and,
said second electrode inserting step includes the step of inserting said second electrode between said nerve fascicles.

16. The method according to claim 15 wherein:
said first electrode inserting step includes the step of inserting said first electrode without penetrating said nerve perineurium membrane at said first longitudinal position; and,
said second electrode inserting step includes the step of inserting said second electrode without penetrating said nerve perineurium membrane at said second longitudinal position.

17. An implantable cuff comprising:
a self-curling sheet adapted to encircle body tissue, the sheet including a first resiliently extensible layer and a second layer bonded to the first layer such that it tends to maintain an interface between the first and second layers extended, such that resilient contractive forces of the first layer bias the sheet to curl into an elongate non-conductive cylindrical sleeve; and,
at least one conductive segment on the self-curling sheet adapted to pierce said body tissue, the conductive segment radially inwardly extending from the self-curling sheet when curled into the elongate cylindrical sleeve.

18. The implantable cuff according to claim 17 further comprising a plurality of radially inwardly extending conductive segments on the self-curling sheet.

19. The implantable cuff according to claim 18 wherein the first resiliently extensible layer and the second layer cooperate to control the bias of the sheet in a manner that said plurality of conductive segments gradually pierce said body tissue over a predefined time period.

20. The implantable cuff according to claim 19 wherein:
the self-curling sheet is adapted to encircle an elongate nerve encased in an epineurium membrane and including at least one longitudinally extending group of axons surrounded by a perineurium membrane forming a fascicle; and,
the first resiliently extensible layer and the second layer cooperate to control the bias of the sheet in a manner that said plurality of conductive segments gradually pierce said epineurium membrane avoiding said perineurium membrane over the predefined time period.

21. The implantable cuff according to claim 17 wherein the first resiliently extensible layer and the second layer cooperate to control the bias of the sheet in a manner that said at least one conductive segment gradually pierces said body tissue over a predefined time period.

22. The implantable cuff according to claim 21 wherein:
the self-curling sheet is adapted to encircle an elongate nerve encased in an epineurium membrane and including at least one longitudinally extending group of axons surrounded by a perineurium membrane forming a fascicle; and,
the first resiliently extensible layer and the second layer cooperate to control the bias of the sheet in a manner that said at least one conductive segment gradually pierces said epineurium membrane avoiding said perineurium membrane over the predefined time period.

23. An interfascicular nerve electrode comprising:
a body member adapted on a first surface to engage an associated external nerve;
a conductive member on the body member; and,
displacing means on said body member for displacing the conductive member into said associated external nerve.

24. The interfascicular nerve electrode according to claim 23 wherein:
said body member is substantially cylindrical and adapted to longitudinally receive said associated external nerve therein; and,
said conductive member is radially inwardly extending from the cylindrical body member.

25. The interfascicular nerve electrode according to claim 24 wherein said displacing means is a deformable resiliently biased portion of said cylindrical body member.

26. The interfascicular nerve electrode according to claim 24 wherein said conductive member comprises a silicon substrate having a conductive portion thereon.

27. A nerve electrode comprising:
a body member;
attachment means for attaching the body member to an associated external nerve;
a conductive member on the body member; and,
means for displacing the conductive member to be within said associated external nerve.

28. The nerve electrode according to claim 27 wherein said displacing means is a deformable resiliently biased portion of said body member.

29. A method of inserting a first member into a nerve surrounded by an epineurium membrane and including at least one fascicle, the method comprising the steps of:
piercing said epineurium membrane with said first member; and,
gradually moving said first member through said epineurium membrane over a predetermined time period while avoiding said fascicle.

30. The method according to claim 29 wherein said moving step includes gradually moving said first member through said epineurium membrane and into said nerve while avoiding piercing a perineurium membrane of said at least one fascicle.

31. The method according to claim 29 wherein said moving step includes moving said first member through said epineurium membrane over said predetermined time period defined by a time period lasting long enough to avoid damage to said nerve.

32. The method according to claim 29 wherein said piercing step includes piercing said epineurium membrane with a first portion of said first member, the first portion being adapted for blunt piercing.

33. The method according to claim 32 further comprising:
piercing said epineurium membrane with a first portion of a second member operatively connected to the first member, the first portion of the second member being adapted for blunt piercing; and,
gradually moving said second member through said epineurium membrane and into said nerve avoiding piercing a perineurium membrane.

34. The method according to claim 33 wherein said first member epineurium piercing step and said second member epineurium piercing step are substantially simultaneously performed.

35. The method according to claim 33 wherein said first member gradually moving step and said second member gradually moving step are substantially simultaneously performed.

36. The method according to claim 35 wherein said first and second member gradually moving steps include moving said first portions of said first and second members through said epineurium membrane and into said nerve avoiding piercing said perineurium membrane over said predetermined time period lasting at least an hour.

37. The method according to claim 29 further comprising:
piercing said epineurium membrane with a second member operatively connected to said first member; and,
gradually moving said second member through said epineurium membrane over at least said predetermined time period while avoiding said fascicle.

38. The method according to claim 29 further comprising:
piercing said epineurium membrane with a plurality of second members operatively connected to said first member; and,
gradually moving said plurality of second members through said epineurium membrane over at least said predetermined time period while avoiding said fascicle.

39. A nerve electrode comprising:
a substantially cylindrical body member formed of a resiliently deformable elastomeric material and adapted to receive an elongate nerve therein;
at least two circumferentially spaced apart longitudinally extending slits defined in said body member to form a resiliently deformable spring member;
at least one piercing member on said resiliently deformable spring member, the at least one piercing member including a portion adapted to penetrate the elongate nerve; and,
at least one conductive member on said at least one piercing member.

40. The nerve electrode according to claim 39 wherein said at least two circumferentially spaced apart longitudinally extending slits defined in said body member form a resiliently deformable spring member joined to said body member at at least one point.

41. The nerve electrode according to claim 40 wherein said at least two circumferentially spaced apart longitudinally extending slits defined in said body member form a resiliently deformable spring member joined to said body member at at least two points.

42. The nerve electrode according to claim 39 wherein:
said substantially cylindrical body member is adapted to engage the elongate nerve on a first inner surface of the cylindrical body member; and,
said at least one piercing member on said resiliently deformable spring member is oriented inwardly radially extending from said first inner surface.

43. A method of manufacturing a nerve electrode comprising:
providing a substantially cylindrical body member formed of a resiliently deformable elastomeric material and adapted to receive an elongate nerve therein;
forming at least two circumferentially spaced apart longitudinally extending slits in said body member to define a resiliently deformable spring member;
disposing at least one piercing member on said resiliently deformable spring member, the at least one piercing member including a portion adapted to enter into the elongate nerve; and,
providing at least one conductive member on said at least one piercing member.

44. The method of manufacturing a nerve electrode according to claim 43 wherein the step of disposing said at least one piercing member on said resiliently deformable spring member includes inserting the at least one piercing member through said body member.

45. The method of manufacturing a nerve electrode according to claim 44 wherein the step of disposing said at least one piercing member on said resiliently deformable spring member includes inserting the at least one piercing member through said resiliently deformable spring member.

46. The method of manufacturing a nerve electrode according to claim 43 wherein the step of forming at least two circumferentially spaced apart longitudinally extending slits in said body member includes forming at least two circumferentially spaced apart longitudinally extending slits in said body member to define a resiliently deformable spring member joined to said body member at at least one point.

47. The method of manufacturing a nerve electrode according to claim 46 wherein the step of disposing said at least one piercing member on said resiliently deformable spring member includes inserting the at least one piercing member through said resiliently deformable spring member.

48. The method of manufacturing a nerve electrode according to claim 43 wherein the step of forming at least two circumferentially spaced apart longitudinally extending slits in said body member includes forming at least two circumferentially spaced apart longitudinally extending slits in said body member to define a resiliently deformable spring member joined to said body member at two points.

49. The method of manufacturing a nerve electrode according to claim 48 wherein the step of disposing said at least one piercing member on said resiliently deformable spring member includes inserting the at least one piercing member through said resiliently deformable spring member.

* * * * *

UNITED STATES PATENT AND TRADEMARK OFFICE
CERTIFICATE OF CORRECTION

PATENT NO. : 5,400,784
DATED : March 28, 1995
INVENTOR(S) : Dominique M. Durand; Dustin J. Tyler It is certified that error appears in the above-indentified patent and that said Letters Patent is hereby corrected as shown below:

On the title page: Item [75] should read as follows: Dominique M. Durand, Solon; Dustin J. Tyler, Cleveland, both of Ohio.

Signed and Sealed this

Sixth Day of June, 1995

BRUCE LEHMAN

*Attest:*

*Attesting Officer*     *Commissioner of Patents and Trademarks*

UNITED STATES PATENT AND TRADEMARK OFFICE
CERTIFICATE OF CORRECTION

PATENT NO. : 5,400,784
DATED : March 28, 1995
INVENTOR(S) : Dominique J. Durand et al.

It is certified that error appears in the above-identified patent and that said Letters Patent is hereby corrected as shown below:

Column 1, before "Background of the Invention", please insert the following paragraph:

---This invention was made with government support under Grant No. NIH NS32845 awarded by the National Institutes of Health. The government has certain rights in this invention.---

Signed and Sealed this

Sixth Day of July, 1999

Attest:

Q. TODD DICKINSON

Attesting Officer

Acting Commissioner of Patents and Trademarks